United States Patent [19]
Kinnersley et al.

[11] Patent Number: 5,153,130
[45] Date of Patent: Oct. 6, 1992

[54] METHOD AND COMPOSITION FOR PLANT TISSUE AND CELL CULTURE

[75] Inventors: Alan M. Kinnersley, Bedford Park; Wayne E. Henderson, Bolingbrook, both of Ill.

[73] Assignee: CPC International Inc., Englewood Cliffs, N.J.

[21] Appl. No.: 871,966

[22] Filed: Jun. 9, 1986

[51] Int. Cl.$^5$ .......... C12N 5/00; C12N 5/02; C12P 1/00
[52] U.S. Cl. .............. 435/240.45; 435/41; 435/240.46; 435/240.48; 435/240.54
[58] Field of Search .......... 435/240, 241, 240.4, 435/240.48, 240.49, 240.54, 41, 240.45, 240.46

[56] References Cited
PUBLICATIONS

Verma et al. 1977, Plant Physiol. 59:81-85.
Button, J. 1978. Z. Pflanzenphysiol. 88:61-68.
Kochba et al. 1973. Z. Pflanzenzüchtg. 69:156-162.
Yamamoto et al. 1981. Biol. Abstr. 73:#78759.
Yamamoto et al. 1981. Chem. Abstr. 95 (19):#165840y.
Fukai, S. 1986. Chem. Abstr. 106 (17):#133687h.
Scannel, et al., "The Regulation of Carbohydrate Metabolism in Animal Cells: Growth on Starch and Maltose", CA. 94, 80971w, 1981.
Rheinwald, et al. "Growth of Cultured Mamalian Cells on Secondary Glucose Sources", CA. 82 29168q, 1975.

*Primary Examiner*—David T. Fox
*Attorney, Agent, or Firm*—Rockey, Rifkin and Rythen

[57] ABSTRACT

Improved secondary metabolite production is achieved by culturing plant tissue and plant cells in a culture medium wherein the carbohydrates comprise a mixture of maltose and glucose.

8 Claims, No Drawings

METHOD AND COMPOSITION FOR PLANT TISSUE AND CELL CULTURE

FIELD OF THE INVENTION

The present invention relates to a method of plant tissue and cell culture which increases cell differentiation and the amount of secondary products produced by the cells.

BACKGROUND OF THE INVENTION

When plant cells are grown outside the plant in synthetic media, undifferentiated cell multiplication, called callus formation, is observed. The cells may also undergo plant cell differentiation with the development in culture of embryos or one or more portions of the plant, generally roots or shoots.

Differentiation of plant tissue culture is of importance in agriculture where rapid plant propagation of tissue culture is independent of seed availability and growing season. Plants produced from tissue culture have uniform characteristics and are free of virus.

Another application of plant tissue culture which depends on cell differentiation is the production of high value chemicals. Accordingly, a method for enhancing plant cell differentiation in cell tissue culture may also be used as an improved method for obtaining such chemical products.

The media on which plant tissue cultures are grown contain a carbohydrate component as the major nutrient. The carbohydrate usually comprises from 80 to 90% by weight of the solid constituents of the media. The preferred carbohydrates for this purpose have been sucrose or glucose. Occasionally, workers have used maltose, lactose, or other simple sugars.

We have now discovered, surprisingly, that if a proper combination of maltose and glucose is used as all or part of the carbohydrate component of the medium, improved cell differentiation of the cell tissue culture is observed. This results not only in enhanced production of roots and shoots, but also in the increased production of secondary chemicals by the cells.

SUMMARY OF THE INVENTION

In accordance with this invention, there is provided an improved process for increasing cell differentiation in cell tissue cultures which comprises culturing a piece of tissue excised from a plant body, or cells obtained by cultivation of tissue excised from a plant body, in a synthetic basal plant tissue culture medium containing carbohydrates and other nutrients required for growth of said cell tissues wherein the carbohydrates comprise from about 20% to about 90% maltose by weight and at least about 10% glucose by weight.

Further, in accordance with this invention, there is provided a medium for the growth of cell tissue culture wherein the carbohydrates of said medium comprise from about 20% to about 90% maltose by weight and at least about 10% glucose by weight.

DETAILED DESCRIPTION OF THE INVENTION

According to the present invention, plant tissues and the cells are cultivated using a culture medium wherein the carbohydrates in said medium comprise from about 20% to about 90% maltose by weight and at least about 10% glucose by weight. The procedures for preparing the culture and culture medium may be identical to those used to form conventional plant tissue cultures. Thus, a known synthetic culture medium containing inorganic salts, micronutrients, vitamins, and hormones, can be used as the basic culture medium, in which the carbohydrate is replaced with the carbohydrate mixture mentioned above.

The carbohydrate component used in the practice of this invention may be obtained in a variety of ways. The desired amounts of dextrose and maltose can be combined to give a mixture with the desired composition. Alternatively, certain starch hydrolyzates, which contain suitable combinations of dextrose and maltose, can be employed. One such starch hydrolyzate which is commercially available from the Corn Products Division of CPC International Inc. bears the trade name GLOBE® 1632. This hydrolyzate contains approximately 35% dextrose and 30% maltose, with the remainder being higher oligosaccharides. Carbohydrate mixtures suitable for use in this invention can also be obtained by mixing various amounts of dextrose and maltose with starch hydrolyzates to give a mixture having the desired amounts of these sugars.

The amount of carbohydrate mixture containing maltose and dextrose to be added to the basal culture medium, in accordance with the present invention, may be in the range of from about 10 grams to about 50 grams, preferably from about 15 grams to about 30 grams, per liter of medium. The culture medium to which the carbohydrate has been added may be used per se for the cultivation. It is permissible, as in a conventional culture, to incorporate further differentiation promoting agents, such as phytohormones, in the medium in accordance with the specific purpose.

The plant tissue to be cultured includes any tissue taken out of an individual plant body, and particularly parts such as shoot apex, cambium, seedling hypocotyl, and the like are preferred. It is also possible to cultivate undifferentiated cells developed in plants, such as callus cells. Tissues or cells resulting from successive cultivation may be used as well.

When a plant tissue is cultivated in a culture medium containing the carbohydrate mixture of this invention, the promotion of differentiation is realized, so that a plant body, stem, leaf, or root can be developed from the callus. It is possible to harvest the cell mass and the grown body or parts, or to transplant the differentiated plant body as a seedling. It may also be possible to extract useful substances from the cells obtained.

As described above, the method according to the present invention permits an efficient cultivation of a plant tissue or cells by enhancing their multiplication and differentiation by adding a proper carbohydrate mixture to the culture medium. By this means, it is possible to harvest the cultivated plants or cells as such, or to extract useful substances from them. It is also possible to obtain homogeneous seedling cultures thereby propagating a particular plant species.

The following examples illustrate certain embodiments of the present invention. Unless otherwise stated, all proportions and percentages are provided on the basis of weight.

EXAMPLE 1

Tobacco plants, *Nicotiana tabacum* L. - cultivar Burley 21, were grown from seed. Leaves were surface-sterilized by immersion in 0.3% NaOCl solution for 20 minutes followed by two washes with distilled water.

Explants were obtained with a 0.6-cm diameter cork borer and were cultured on a basic culture medium solidified with 0.9% agar. The composition of the medium is given in Table I.

TABLE I

| BASIC CULTURE MEDIUM (pH 5.7) | |
| --- | --- |
| | Milligrams/Liter |
| $NH_4NO_3$ | 1,650 |
| $KNO_3$ | 1,900 |
| $CaCl_2.2H_2O$ | 440 |
| $MgSO_4.7H_2O$ | 370 |
| $KH_2PO_4$ | 170 |
| $Na_2EDTA$ | 37.3 |
| $FeSO_4.7H_2O$ | 27.8 |
| $H_3BO_3$ | 6.2 |
| $MnSO_4.H_2O$ | 16.9 |
| $ZnSO_4.7H_2O$ | 8.6 |
| KI | 0.83 |
| $Na_2MoO_4.2H_2O$ | 0.25 |
| $CuSO_4.5H_2O$ | 0.025 |
| $CoCl_2.6H_2O$ | 0.025 |
| Sucrose | 30,000 |
| i-Inositol | 100.0 |
| Nicotinic Acid | 0.5 |
| Pyridoxine.HCl | 0.5 |
| Thiamine.HCl | 0.1 |
| alpha-Naphthaleneacetic Acid | 2.0 |
| Kinetin | 0.2 |

The cells formed calli when grown on the solid media in test tubes in the dark at 25° C. for 2 months. Suspension cultures were initiated from the calli by first dispersing the callus tissue in liquid medium using a rolled tube on a rotating drum and then transferring a 2–5-ml aliquot of the suspension to a 250-ml Erlenmeyer flask containing 50 ml of fresh medium. Flasks were kept in darkness at room temperature on a gyrotary shaker at 100 rpm. Three to four flasks of each culture were maintained. The suspension cultures were subcultured approximately every 20 days into fresh growth medium. During several months of serial passage, nicotine was not detected in the tissue cultures.

Nicotine analysis was performed by taking a 8- or 16-ml aliquot of a suspension culture, mixing it with 10 ml of 5M NaOH, and steam distilling the mixture. The steam distillate was collected in 5 ml of 0.5M HCl and the nicotine content of the distillate was determined spectrophotometrically by measuring the ultraviolet absorption at 236, 259, and 282 nm. Nicotine content was calculated from the absorbances by standard methods as reported by Willits, et al, *Anal. Chem.*, 22, 430–433 (1950).

Cells which had grown under the above conditions for 8 months were transferred into growth media which contained a starch hydrolyzate in place of the sucrose. This starch hydrolyzate contained 37% glucose, 29% maltose, and 34% of higher oligosaccharides. Control cultures were run using sucrose as the carbohydrate in the medium. Cultures containing both media were subcultured at approximately 20-day intervals, and aliquots of the suspension cultures were analyzed for nicotine at each harvest date. The results given in Table II, which are the average of three or four cultures in each case, show that only the starch hydrolyzate containing a mixture of glucose and maltose produced appreciable quantities of nicotine.

TABLE II

| TOBACCO SUSPENSION CULTURES GROWN ON SUCROSE AND STARCH HYDROLYZATE | | | | |
| --- | --- | --- | --- | --- |
| | Tissue (g/l Dry Basis) | | Nicotine (% of Tissue Dry Basis) | |
| Harvest No. | Sucrose in Medium | Starch Hydrolyzate in Medium | Sucrose in Medium | Starch Hydrolyzate in Medium |
| 1 | 12.1 | 7.1 | 0.219 | 0 |
| 2 | 11.1 | 13.1 | 0 | 0 |
| 3 | 6.1 | 9.5 | 0 | 0.255 |
| 4 | 15.1 | 16.6 | <0.05 | 0.843 |
| 5 | 7.2 | 5.56 | <0.05 | 0.17 |
| 6 | 7.1 | 6.81 | <0.05 | 3.2 |
| 7 | 14.3 | 12.8 | 0 | 0.53[a] |
| 8 | 17.6 | 11.1 | 0 | 0.23 |
| 9 | 16.5 | 10.8 | <0.05 | 1.45 |

[a] Cultures were exposed to excessive temperature during this passage due to failure of a gyrotary shaker.

EXAMPLE 2

The general procedure of Example 1 was followed in which the carbohydrate was either pure glucose, pure maltose, or mixtures of these. The cells grew poorly on maltose and produced no measurable amount of nicotine. The cells grew well on glucose but produced only small amounts of nicotine. The yields of nicotine by cells grown on glucose were similar to those produced by cells grown on sucrose given in Example 1. The results given in Table III show that mixtures of glucose and maltose, and starch hydrolyzates containing mixtures of glucose and maltose, within the ranges disclosed in this invention, can be used to grow tobacco tissue cultures which produce surprisingly high levels of nicotine.

TABLE III

| TOBACCO SUSPENSION CULTURES GROWN ON VARIOUS CARBOHYDRATES | | | | | | |
| --- | --- | --- | --- | --- | --- | --- |
| | Nicotine (% of Tissue Dry Basis) | | | | | |
| Harvest No. | Glucose | 15% Glucose 85% Maltose | 25% Glucose 75% Maltose | 50% Glucose 50% Maltose | Hydrolyzates A[a] | B[b] |
| 1 | — | — | 0.44 | 0.22 | 0.40 | 0.16 |
| 2 | 0.001 | — | 0.037 | 0.42 | 0.028 | — |
| 3 | 0.059 | 1.34 | 0.38 | 1.41 | 1.67 | — |
| 4 | 0.074 | 1.37 | 1.49 | 2.59 | 0.40 | 0.023 |
| 5 | 0.038 | 4.24 | 4.34 | 4.26 | 2.77 | 0.84 |
| 6 | 0.15 | 5.04 | 5.02 | 4.68 | 4.33 | 0.86 |

[a] A starch hydrolyzate containing 37% glucose, 29% maltose, and 34% higher oligosaccharides.
[b] A starch hydrolyzate containing 25% glucose, 19% maltose, and 56% higher oligosaccharides--comparative test, not an example of this invention.

EXAMPLE 3

Suspension cultures of wild carrot (*Daucus carota* L.) were grown using the same procedure as used for the suspension cultures of tobacco cells in Example 1. The medium used was the wild carrot medium of Wetherell,

*Plant Physiology*, 44, 1734–1737 (1969) as given in Table IV. Again, the suspension cultures were subcultured approximately every 20 days into fresh growth medium.

TABLE IV

WILD CARROT MEDIUM (pH 5.8)

| | Milligrams/Liter |
|---|---|
| $KNO_3$ | 4,000 |
| $NH_4Cl$ | 540 |
| $MgSO_4.7H_2O$ | 185 |
| $CaCl_2.2H_2O$ | 220 |
| $KH_2PO_4$ | 68 |
| $Na_2EDTA$ | 18.6 |
| $FeSO_4.7H_2O$ | 13.6 |
| $MnSO_4.H_2O$ | 7.0 |
| $ZnSO_4.7H_2O$ | 4.0 |
| $H_3BO_3$ | 2.4 |
| $(NH_4)_6Mo_7O_{24}.4H_2O$ | 0.01 |
| KI | 0.38 |
| $CuSO_4.5H_2O$ | 0.015 |
| Thiamine.HCl | 3.0 |
| Carbohydrate | 20,000 |
| 2,4-Dichlorophenoxyacetic Acid | 0.5 |

Anthocyanin pigment produced by the carrot cells was determined by the following analytical technique. Five-ml aliquots of the suspension culture were diluted with 2 volumes of water before the cells were collected by centrifugation. The cells were extracted with 10 ml of a solution containing 95% methanol, 4% water, and 1% hydrochloric acid by volume. Extractions were performed at room temperature overnight. These mixtures were centrifuged and the absorbances of the bright pink solutions were determined at 530 nm against a solvent blank. The results, using various carbohydrates in the medium, are given in Table V where the relative pigment production of the various cell cultures are indicated by the absorbance per 100 ml of culture. They clearly show that cultures containing carbohydrates with the proportions of maltose and dextrose specified in this invention cause differentiation of the wild carrot cells with enhanced and more rapid production of pigment over those given by cells grown on media containing the single carbohydrates: sucrose, glucose, or maltose.

TABLE V

WILD CARROT SUSPENSION CULTURES GROWN ON VARIOUS CARBOHYDRATES

| | Anthocyanin Pigment ($A_{530}$/100 ml) | | | | |
|---|---|---|---|---|---|
| Harvest No. | Sucrose | Glucose | Maltose | 52% Glucose 48% Maltose[a] | Starch Hydrolyzate[b] |
| 1 | 2.49 | 3.53 | 2.7 | 7.4 | 7.2 |
| 2 | 3.20 | 3.53 | 6.5 | 8.8 | 9.5 |

[a]Used at a level of only 12 g/l of medium.
[b]Contains 37% glucose, 29% maltose, and 34% higher oligosaccharides.

EXAMPLE 4

Suspension cultures of an embryogenic wild carrot cell line were grown on the medium given in Table IV except that the 2,4-dichlorophenoxyacetic acid was omitted. This allowed the cultures to form embryos. After two subcultures on a medium containing a given carbohydrate, the embryos were separated from the medium, washed with water, and dried. The results given in Table VI show that the starch hydrolyzate, which contains proportions of maltose and dextrose within those specified in this invention, caused increased embryo production over those given by cells grown on media containing the single carbohydrates: sucrose, glucose, or maltose.

TABLE VI

WILD CARROT SUSPENSION CULTURES GROWN ON VARIOUS CARBOHYDRATES

| Embryo Weight (mg)[a] | | | |
|---|---|---|---|
| Sucrose | Glucose | Maltose | Starch Hydrolyzate[b] |
| 222 | 182 | 307 | 339 |

[a]Each value is the average weight from three separate cultures.
[b]Contains 37% glucose, 29% maltose, and 34% higher oligosaccharides.

Thus, it is apparent that there has been provided, in accordance with the invention, an improved medium for plant tissue culture. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for increasing secondary metabolite production in cell tissue cultures which comprises culturing a piece of tissue excised from a plant body, or cells obtained by cultivation of tissue excised from a plant body, in a synthetic basal plant tissue culture medium comprising a mixture of carbohydrates and other nutrients required for growth of said cell tissues wherein from about 20% to about 90% by weight of the mixture of carbohydrates consists of maltose and at least about 10% by weight of the mixture of carbohydrates consists of glucose and wherein carbohydrates other than maltose and glucose comprise from about 0% to about 34% by weight of the mixture of carbohydrates.

2. A process according to claim 1 wherein the culture medium comprises from about 5 grams to about 50 grams of the mixture of carbohydrates per liter of said culture medium.

3. A process according to claim 1 wherein the mixture of carbohydrates comprises a starch hydrolyzate.

4. The process of claim 1 wherein the cell tissue culture is a tobacco cell tissue culture.

5. The process of claim 1 wherein the tissue culture is a wild carrot tissue culture.

6. A medium for increasing secondary metabolite production in cell tissue cultures comprising a synthetic basal plant tissue culture medium having a mixture of carbohydrates and other nutrients required for growth of said cell tissues wherein from about 20% to about 90% by weight of the mixture of carbohydrates consists of maltose and at least about 10% by weight of the mixture of carbohydrates consists of glucose and wherein carbohydrates other than maltose and glucose comprise from about 0% to about 34% by weight of the mixture of carbohydrates.

7. A medium of claim 6 wherein the mixture of carbohydrates comprises from about 5 grams to about 50 grams per liter of said medium.

8. A medium of claim 6 wherein the mixture of carbohydrates comprises a starch hydrolyzate.

* * * * *